United States Patent [19]

Sovak et al.

[11] 4,389,526

[45] Jun. 21, 1983

[54] INTERMEDIATES AND SYNTHESIS OF 2-AMINO-2-DEOXYTETRITOLS

[75] Inventors: Milos Sovak, La Jolla; Ramachandran Ranganathan, San Diego, both of Calif.

[73] Assignee: The Regents of the University of California, Berkeley, Calif.

[21] Appl. No.: 289,743

[22] Filed: Aug. 3, 1981

[51] Int. Cl.³ .................................................. C07D 321/06
[52] U.S. Cl. ......................................... 549/347; 549/228; 549/415; 549/472; 564/488; 564/490; 564/503; 564/504
[58] Field of Search ............... 260/338; 564/488, 490, 564/503, 504; 549/347, 415, 472

[56] References Cited

U.S. PATENT DOCUMENTS

| | | | |
|---|---|---|---|
| 3,530,153 | 9/1970 | Potts et al. | 564/488 X |
| 3,558,711 | 1/1971 | Eckert et al. | 564/490 |
| 3,574,760 | 4/1971 | Sasaki et al. | 564/488 |
| 3,652,594 | 3/1972 | Pawloski | 260/338 |
| 3,944,619 | 3/1976 | Singh | 564/488 |
| 3,966,768 | 6/1976 | Pawloski | 260/338 |
| 4,110,101 | 8/1978 | Stach et al. | 260/338 |
| 4,132,642 | 12/1978 | Miller | 564/488 |

*Primary Examiner*—Ethel G. Love
*Attorney, Agent, or Firm*—Bertram I. Rowland

[57] ABSTRACT

Novel methods are provided for synthesizing 2-amino-2-tetritol, by positive halogen addition to protected 1,4-dioxybutene-2 in the presence of a nitrile, resulting in addition of a halo functionality and the nitrile functionality across the double bond. Upon hydrolysis, the desired erythro-product can be obtained in stereochemically good yield.

9 Claims, No Drawings

INTERMEDIATES AND SYNTHESIS OF 2-AMINO-2-DEOXYTETRITOLS

The invention described herein was made in the course of work under a grant from the Department of Health and Human Services.

BACKGROUND OF THE INVENTION

1. Field of the Invention

In many areas of chemistry, it is desirable to find simple synthetic procedures for preparing compounds. In most situations where stereoisomers are involved, any procedure should provide for the preparation of the particular desired isomer with minimal contamination of the undesired stereoisomer. The synthetic procedure is frequently only difficultly realized where the compound of interest is highly functionalized.

D,L-2-Amino-2-deoxyerythritol ("2-aminoerythritol") is of interest in the preparation of X-ray contrast media. See, for example, co-pending application Ser. No. 141,097, filed Apr. 17, 1980, now U.S. Pat No. 4,341,756. The stereoisomeric threitol can be prepared from the olefin employing conventional protective groups and conventional trans-addition, but the erythro derivative requires cis-addition which does not occur directly. Furthermore, with many synthetic sequences the presence of heterofunctionalities can lead to by-products, including degradation products. It therefore becomes a difficult problem to find a synthetic approach which permits the employment of inexpensive starting materials to produce a highly functionalized compound in good yield substantially free of an undesired stereoisomer.

2. Description of the Prior Art

Cairns et al, J. Org. Chem., 17, 751 (1952) teaches the addition of positive chlorine and a nitrile across a double bond to produce a halo-amide. Co-pending application Ser. No. 141,097, filed Apr. 17th, 1980 has a description of the preparation of erythritylamine by inversion of threitylamine. Also disclosed in that application are X-ray contrast media employing the subject aminotetritols.

SUMMARY OF THE INVENTION

D,L-2-Amino-2-deoxyerythritol and derivatives thereof are prepared in high yield substantially free of the undesired stereoisomer. The economical 1,4-dihydroxybutene-2 is employed as the starting material. The hydroxyl groups are protected in conventional manners and the halo-amide formed by addition of halogen and a nitrile group at nitrogen across the double bond under conditions where the protective groups are maintained and trans-addition occurs. Upon hydrolysis, including removal of the protective groups, the 2-aminoerythritol results. In some situations, it is desirable to retain the hydroxyl protective groups, where further derivitization of the amino group is to be carried out.

DESCRIPTION OF THE SPECIFIC EMBODIMENTS

Starting with 1,4-dihydroxybutene, 2-aminoerythritol or derivatives thereof are prepared. Acid labile hydroxyl protective groups are employed to protect the hydroxyl groups during the subsequent steps of the synthetic sequence. The protected diol is combined with a source of positive halogen in the presence of a nitrile to provide for trans-addition of the halogen and the nitrile. The nitrile becomes bonded at nitrogen to form an imidoyl halide, which is preferably hydrolyzed to the corresponding amide without isolation. Upon treatment with an hydroxyl source, depending upon the nature of the source, the halo-amide or derivative thereof, will be produced or in the presence of water and a tertiary-amine, one can proceed in a single state to the 2-aminoerythritol compound with the 1- and 4-hydroxyl groups protected. Depending upon the nature of these groups, they may be removed in conventional ways at an appropriate point in the reaction sequence to the desired product.

The reaction sequence may be generally depicted as follows:

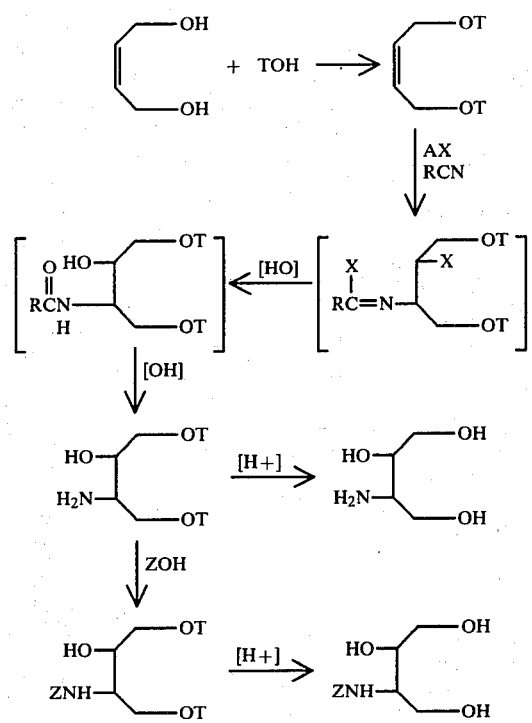

T is an acid labile protective group wherein 2Ts may be taken together to form a ring;

X is halogen of atomic number 17 to 80, more usually chlorine or bromine;

A is a heteroatom containing group, which may be the same or different from X and includes halogen, oxy e.g. hydroxyl and alkoxy, amido and azaheterocycles, to provide X as a positive halogen; A is therefore the same or of greater electronegativity than X;

R is hydrogen or an organic group free of interfering functionalities, such as aliphatic unsaturation, generally from about 1 to 12 carbon atoms, more usually of from about 1 to 4 carbon atoms, preferably from about 1 to 2 carbon atoms. Usually, R will be aliphatic, alicyclic or aromatic, generally free of heterofunctionalities. For economic reasons, R will normally be methyl; and Z is an acyl group, where the amide compounds find particular use in the preparation of X-ray contrast media.

The first step in the synthetic procedure is the protection of the hydroxyl group of the commercially available 1,4-dihydroxybutene-2. Any convenient protective group may be employed and numerous groups are well known in the literature. While it is not essential that an acid labile protective group be employed, for the most part these will be the most economic and convenient. Therefore, they will normally be the ones of choice. Usually, the protective group will form an ether or ester, particularly ethers. Ethers can be prepared as acetals or ketals, where mono or di-acetals or -ketals are formed. In the event of a monoacetal or -ketal, a 1,3-dioxacycloheptane will be formed. Alternatively, diacetals or -ketals may be formed by employing vinylethers, such as dihydrofuran or dihydropyran, or a haloalkylether e.g. chloromethyl ether. alpha-Substituted benzyl compounds can also be employed as protective groups. Other groups include orthoesters, carbonates, and thiocarbonates, where the protective groups provide a cyclic compound.

The various ethers and esters may be formed with acid or base catalysis, where the particular methods of preparing the protected diol are well known in the literature. See for example, Wagner and Zook, Synthetic Organic Chemistry, John Wiley and Sons, N.Y. 1953. The important aspects of the protective group is that it is readily prepared, does not interfere with the subsequent steps involved with the synthetic procedure, while being stable under the conditions employed in the subsequent steps and is readily removable when necessary. Desirably, the protective group should be removable under mildly acidic or basic conditions.

The protected butenediol is then contacted under mild conditions with a source of positive halogen, where the halogen is of atomic number 17 to 80, particularly chloro or bromo, in the presence of a nitrile group, which may be bonded to hydrogen or an organic radical which is free of interfering substituents. Conveniently, the nitrile may also be the solvent, where the nitrile is a liquid at the temperature of the reaction. Generally, the temperature will be at ambient or below, generally below about 20° C., more usually below about 0° C. and not less than about −70° C., preferably not less than about −30° C. Various sources of positive halogen can be used, such as chlorine, bromine, hypochlorite, hypobromite, N-chlorosuccinimide, cyanogen chloride, cyanogen bromide, cyanuryl bromide, etc. The particular group to which the positive halogen is bound is limited by not interfering with the addition of the nitrile to the olefin. Therefore, the positive halogen compounds which are chosen will be selected so as to be incapable of competing with the nitrile group under the conditions of the reaction.

The choice of the nitrile is primarily one of convenience. As already indicated, it may be conveniently provided as the solvent, so as to be present in high concentration. Furthermore, since the nitrile group is only a source of amino, the particular group bonded to the nitrile group will be lost in the procedure. Therefore, based on considerations of economy and efficiency, while any nitrile compound can be used, normally the group bonded to the nitrile will be hydrogen or of from about 1 to 12 carbon atoms, normally hydrocarbon, and particularly methyl. Acetonitrile fulfills substantially all of the requirements for a source of a nitrile group.

Depending upon the nature of the positive halogen, it may be necessary to add an unreactive base, where a hydrohalide is formed. By unreactive is intended unable to react with alkyl halogen to form an isolatable product under the conditions of the reaction. A wide variety of tertiary amines may be employed, such as trimethylamine, pyridine, picoline, triethylamine, or the like. Desirably, stoichiometric amounts of water are also included, so that the imidolyl halide which is formed is rapidly hydrolysed to the amide and the hydrohalide acid is neutralized by the tertiary base. In this manner, the halo-amide derivative may be prepared directly from the olefin in a single step without isolation of any of the intermediates.

The concentration of the olefin in the solvent may be varied widely, generally ranging from about 0.1 M to about 5 M, more usually from about 0.2 M to 5 M. The positive halogen will be present in at least stoichiometric amounts and generally in minor excess, usually not more than about 3-fold excess, more usually not more than about 2-fold excess. The excess will depend upon the activity of the halogen and its involvement in side reactions. Where a hydrohalide is formed, the amount of the base will be at least stoichiometric, usually at least about 1.2-fold greater than stoichiometric and may be 2-fold or more in excess. The amount of water which is employed for in situ hydrolysis will be at least stoichiometric and may be in minor excess, generally not exceeding 2-fold excess.

The time for reaction will vary widely, depending upon the reactivity of halide. Usually, the time will not be greater than about 12 hours, more usually not exceeding about 6 hours. The various reactants may be added incrementally, so long as the appropriate ratios are maintained, or all at once. Desirably, where chlorine or bromine are employed, the halogen will be added incrementally.

After completion of the reaction, the halo-amide which is trans-halo-acylamide, may then be isolated and treated with a mild base at elevated temperatures, generally exceeding about 60° C., more usually exceeding about 75° C. and below about 150° C., usually below about 135° C. At temperatures above the boiling point of water, the reaction is carried out in a sealed system. The pH of the system will normally be about 7.5 to 10, more usually about 8 to 9.5. Various bases may be used, conveniently alkali metal salts, such as sodium carbonate, sodium borate, sodium phosphate, or the like. After sufficient time to hydrolyse the halogen, the amide group may be hydrolysed in accordance with conventional techniques. Most conveniently, the pH may be increased, generally in excess of 10, and the hydroxide concentration may be as high as about 1 M in this deacylation step. Elevated temperatures will be employed, generally in excess of 60° C., and below about 150° C., more usually from about 90 to 135° C. After sufficient time for complete hydrolysis of the amide, cis-hydroxy-acylamide, the protected 2-aminoerythritol may then be isolated and used for preparation of other compounds or the protective groups removed as desired.

The subject compounds find particular use in the preparation of X-ray contrast media.

Of particular interest are contrast media compounds having the following formula:

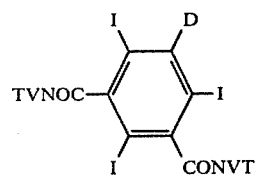

wherein:

D is —CONVT or —NVCOE;

T is trihydroxybutyl, particularly 1,3,4-trihydroxybutyl-2;

V is hydrogen or lower alkyl of from 1 to 2 carbon atoms, e.g. methyl or ethyl; and E is hydrogen or an alkyl group of from one to three, usually one to two carbon atoms having from zero to two, usually zero to one oxy groups, which are hydroxyl or ether groups of from one to two carbon atoms, preferably one carbon atom; or, two Es may be taken together to provide a linking grop which may be a bond or an alkylene group of from one to four, preferably from one to two carbon atoms and having from zero to four, usually zero to two oxy groups of from zero to two carbon atoms, particularly hydroxy and alkoxy of from one to two carbon atoms.

Illustrative E groups are methyl, ethyl, hydroxymethyl, 1- or 2-hydroxyethyl, 1,2-dihydroxyethyl, or the like. When two Rs are taken together to form a linking group, illustrative linking groups include methylene, ethylene, butylene-1,4, 1,2-dihydroxyethylene, 1,2-dimethoxyethylene, propylene, and 2-oxapropylene.

The aminotetritol may be acylated in accordance with conventional techniques. Conveniently, active acyl groups may be used, such as the halide, mixed anhydride, active ester e.g. N-hydroxy succinimide, or the like. The particular mode of acylation is not critical to this invention.

The protective group may then be removed by any convenient means, conveniently acid hydrolysis.

The X-ray contrast media will normally be employed in combination with a pharmaceutically acceptable carrier, wherein the contrast media compound will be present in concentrations of about 20–500 mg I/ml, more usually 100–400 mg I/ml. The type and quantity of contrast agent to be administered is preferably such as to stay in the system only for about 2 to 3 hrs., although both shorter and longer residence times are normally acceptable.

Besides use as contrast media, the contrast media because of their high molecular weight and density, may find uses for a variety of other purposes. The subject compounds can be used in biological techniques, where cells are handled in solutions of high specific gravity, for example, in centrifugation or differential flotation, since their low osmolality reduces the osmotic lysis of the cells as compared to ionic compounds.

The following examples are offered by way of illustration and not by way of limitation.

EXPERIMENTAL

1. trans-5-Acetylamino-6-Chloro-2,2-Dimethyl-1,3-Dioxepane with —OCl.

4,7-Dihydro-2,2-dimethyl-1,3-dioxepin (I) (12.8 g, 0.10 mole) was dissolved in acetonitrile (50 ml; 1 mole) containing water (1.8 g, 0.1 mole). The solution was cooled to 5° C. and, with rapid stirring, carbon dioxide was bubbled into it in a rapid stream. Finely powdered calcium hypochlorite (64%; 11.6 g, 0.052 mole) was added portionwise at such a rate that the temperature of the reaction mixture was maintained below 15° C. The mixture was stirred for 2 hours after the addition was over. The small excess of hypochlorous acid was destroyed by the addition of a mixture of 1 M sodium bisulfite and 1 M sodium bicarbonate (1:1; 10 ml) until the reaction mixture was negative to the starch-potassium iodide test. The mixture was filtered and the insoluble calcium salts washed with acetonitrile. The solvent was removed in vacuo. The resulting white residue was suspended in carbon tetrachloride, stirred and then filtered to obtain the chloroamide (II) as white crystalline needles (9.75 g, 0.044 mole), (yield 45%), m.p. 150°–51°.

The filtrate was freed of the solvent to obtain the chlorohydrin (III) as a syrupy liquid (8.0 g, 0.044 mole), yield 44%.

2. cis-5-Amino-2,2-Dimethyl-6-Hydroxy-1,3-Dioxepane

A solution of sodium carbonate (48 g, 0.45 mole) in water (400 ml) was heated in a 120° C. oil bath and with efficient mechanical stirring the trans-chloroamide (II) (76 g, 0.34 mole) was added portionwise, as rapidly as possible, such that the foaming due to the evolution of carbon dioxide is under control. The solid went into solution slowly and the solution was refluxed for 1.5 hr., when conversion into the cis-hydroxyamide was complete. 50% Aqueous sodium hydroxide (50 ml, 0.6 mole) was added and the solution was refluxed, with a constant slow flow of nitrogen for 4 hr. The solution was cooled in ice and the pH adjusted to 11.0 by the addition of 2.5 M HCl (120 ml). The solvent was removed in vacuo and the residue was extracted with methylene chloride (4×200 ml). Concentration of the combined methylene chloride extracts, followed by the addition of a small amount of hexane, yielded cis-aminohydroxydioxepane as white crystalline needles (40.7 g, 0.25 mole) (yield 74%), m.p. 102°–103°.

3. cis-5-Amino-2,2-Dimethyl-6-Hydroxy-1.3-Dioxepane (IV) with $Cl_2$

Dry chlorine gas was passed into a stirred solution of 4,7-dihydro-2,2-dimethyl-1,3-dioxep-5-ene (I) (131.7 g, 1.03 mole) in acetonitrile (500 ml) at such a rate that the reaction mixture was maintained at a temperature of −35° to −40°, during 75'. The supply of chlorine was stopped as soon as the reaction mixture became faintly yellow colored and the exothermic reaction ceased. Dry nitrogen was then bubbled into the reaction mixture at −20° for 20', when it became colorless. A mixture of triethylamine (154 ml; 1.13 mole), water (19 ml; 1.05 mole) and acetonitrile (20 ml) was added to the reaction mixture at such a rate that the temperature was maintained below −30°. The thick, pasty mixture was stirred at 0° for 45'. TLC examination indicated the formation of the trans-5-acetamido-6-chloro-2,2-dimethyl dioxepane (II).

The above reaction mixture was added during 25' to a mechanically stirred refluxing solution of $Na_2CO_3$ (212 gm; 2 mole) in water (650 ml). Acetonitrile and triethylamine were removed from the reaction mixture by distillation and the residue refluxed for 5 hr., when conversion into the cis-hydroxyamide (III) was complete. 50% Aqueous sodium hydroxide (88 ml; 1.1 mole) was added and the solution was refluxed under a nitrogen atmosphere for 5.5 hr. The solution was cooled and then continuously extracted with methylene chloride until the aqueous layer was free from the amine product (IV). The methylene chloride solution was dried ($MgSO_4$) and the product crystallized out by the addition of hexane to the boiling methylene chloride solution. The cis-hydroxyamine product (IV) was obtained as crystalline needles (97 g) (yield 60%), m.p. 101°–103°.

4. trans-5-Acetylamino-6-chloro-2,2-dimethyl-1,3-dioxepane (II) with $Cl_2$

Dry chlorine gas was passed into a stirred solution of 4,7-dihydro-2,2-dimethyl-1,3-dioxep-5-ene (I) (64.0 g, 0.5 mole) in acetonitrile (260 ml) at such a rate that the reaction mixture was maintained at a temperature of −35° to −40°, during 50′. The supply of chlorine was stopped as soon as the reaction mixture became faintly yellow colored and the exothermic reaction ceased. The excess chlorine was removed by bubbling dry nitrogen into the reaction mixture at −20° for 15′. A mixture of triethylamine (77 ml; 0.55 mole), water (9 ml; 0.5 mole) and acetonitrile (10 ml) was added to the reaction mixture at such a rate that the temperature was maintained below 0°. The thick, pasty mixture was stirred at 0° for 1 hr. and then freed of the solvent in vacuo. The residue was dissolved in methylene chloride (500 ml) and washed with brine (4×100 ml). The organic layer was dried ($MgSO_4$) and removal of the solvent, followed by drying in vacuo, gave a brown residue (101 g) which was crystallized from methylene chloride-hexane mixture to obtain the product (II) as crystalline needles. 79.9 g (72% yield), m.p. 150°–53°.

5. cis-5-Amino-2,2-dimethyl-6-hydroxy-1,3-dioxepane (IV)

To a mechanically stirred refluxing solution of $Na_2CO_3$ (116.6 g, 1.1 mole) in water (850 ml), the trans-chloroamide (II) (219 g, 0.987 mole) was added portionwise, such that the foaming due to evolution of carbon dioxide is under control. The reaction mixture became a clear solution in 2 hr. and the solution was refluxed for an additional 1.5 hr., when conversion into the cis-hydroxyamide (III) was complete. 50% Aqueous sodium hydroxide (80 ml, 1 mole) was added and the solution was refluxed under nitrogen atmosphere for 4.5 hr. The solution was cooled in ice and the pH adjusted to 11.0 by the addition of 2 M HCl. The solvent was removed in vacuo and the residue azeotroped with toluene thrice to remove traces of water. The dry residue (402 g) was extracted with hot methylene chloride (4×250 ml). The combined organic extracts were concentrated and crystallization of the product was achieved by the addition of hexane to the boiling solution and then cooling it in ice. The hydroxyamine (IV) was obtained as crystalline needles (89 g) (yield 56%), m.p. 103°–4°. A second crop (12 g) (m.p. 99°–101°) of the product increased the yield to 63%.

It is evident from the above results that a simple efficient way is provided for producing erythro-2-amino-2-deoxytetritols. The method requires protection of the hydroxyls of the 1,4-dihydroxybutene. Upon contacting the olefin with a source of positive halogen in the presence of a nitrile, plus a base and water, the erythro compound can be obtained directly in high yield and in pure form. The desired aminotetritol can then be freed of the protective groups or the protective tetritol used in subsequent reactions and the protective groups removed subsequently. The subject invention provides for a simple and practical route to precursors for X-ray contrast media.

The preparation of the contrast media is amply described in copending application Ser. No. 141,097, filed Apr. 17, 1980, as well as U.S. Pat. No. 4,239,747. The acyl halide or other active acyl group may be combined with the 2-aminoerythritol in an inert organic polar medium at mildly elevated temperatures and the reaction allowed to go to completion. The product may then be isolated in accordance with conventional ways.

Although the foregoing invention has been described in some detail by way of illustration and example for purposes of clarity of understanding, it will be obvious that certain changes and modifications may be practiced within the scope of the appended claims.

What is claimed is:

1. A method for preparing a 1,4-dihydroxyl protected -2-amino-2-deoxyerythritol which comprises:
    combining a source of positive halogen of atomic number 17 to 80, a nitrile, aqueous base unreactive with alkylhalogen under the conditions of the reaction, and hydroxyl protected 1,4-dihydroxybutene-2 under mild conditions whereby trans-halo-acylamido is formed;
    treating the trans-halo-acylamido with a mild aqueous base at an elevated temperature to produce cis-hydroxy-acylamido; and
    treating the cis-hydroxy-acylamido with a basic deacylating agent above about 60° C. to produce the desired 1,4-dihydroxyl protected-2-amino-2-deoxyerythritol.

2. A method according to claim 1, wherein said source of positive halogen is of atomic number 17 to 80.

3. A method according to claim 2, wherein said source of positive halogen is a chlorine molecule.

4. A method according to claim 2, wherein said source of positive halogen is hypochlorite.

5. A method according to any of claims 1 or 2, wherein said nitrile is an organic nitrile.

6. A method according to claim 5, wherein said organic nitrile is acetonitrile.

7. A method according to any of claims 1 or 2, wherein said aqueous base in said first step is tertiary amine.

8. A method according to any of claims 1 or 2, wherein said aqueous base in the first step is sodium carbonate.

9. A method according to any of claims 1 or 2, wherein said deacylating agent is a strong base.

* * * * *